United States Patent
Schwender et al.

(10) Patent No.: US 6,281,212 B1
(45) Date of Patent: *Aug. 28, 2001

(54) CHEMOKINE RECEPTOR ANTAGONISTS AND METHODS OF USE THEREFOR

(75) Inventors: Charles F. Schwender, Glen Gardner, NJ (US); Charles R. Mackay, Watertown, MA (US); Julia C. Pinto, Beverly Farms, MA (US); Walter Newman, Boston, MA (US)

(73) Assignee: Millennium Pharmaceuticals, Inc., Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/891,518

(22) Filed: Jul. 11, 1997

Related U.S. Application Data

(60) Provisional application No. 60/021,716, filed on Jul. 12, 1996.

(51) Int. Cl.[7] .................. A61K 31/495; A61K 31/44; A61K 31/55
(52) U.S. Cl. .............. 514/252.13; 514/340; 514/345; 514/347; 514/350; 514/212; 514/213; 514/217
(58) Field of Search .................... 514/255, 340, 514/345, 347, 350, 212, 213, 217

(56) References Cited

U.S. PATENT DOCUMENTS

| | | | |
|---|---|---|---|
| 3,770,729 | 11/1973 | Nakanishi et al. | 260/240 |
| 3,907,812 | 9/1975 | Yamamoto et al. | 260/293.77 |
| 3,922,266 | 11/1975 | Katsube et al. | 260/240 |
| 3,936,468 | 2/1976 | Yamamoto et al. | 260/293.84 |
| 4,012,514 | 3/1977 | Katsube et al. | 424/267 |
| 4,086,234 | 4/1978 | Dryden, Jr. et al. | 260/268 |
| 4,125,612 | 11/1978 | Sherlock | 424/250 |
| 4,250,176 | 2/1981 | Vandenberk et al. | 424/250 |
| 5,116,863 | 5/1992 | Oshima et al. | 514/450 |
| 5,143,922 | 9/1992 | Oshima et al. | 514/320 |
| 5,258,274 | 11/1993 | Helland et al. | 430/522 |
| 5,874,428 | 2/1999 | Dørwald et al. | 514/217 |

FOREIGN PATENT DOCUMENTS

| | | |
|---|---|---|
| 2028031 | 10/1989 | (CA) . |
| 240 698 | 6/1987 | (CS) . |
| 268400 | 5/1991 | (CS) . |
| 0226448A2 | 6/1987 | (EP) . |
| 0307951A2 | 3/1989 | (EP) . |
| 0332064A2 | 3/1989 | (EP) . |
| 342035 | 5/1989 | (EP) . |
| 0400348A1 | 12/1990 | (EP) . |
| 0457701A1 | 5/1991 | (EP) . |
| 0434093A1 | 6/1991 | (EP) . |
| 0533056A2 | 9/1992 | (EP) . |
| 0540165A1 | 5/1993 | (EP) . |
| 0587050A1 | 9/1993 | (EP) . |
| 0596692A2 | 5/1994 | (EP) . |
| 0694543A1 | 7/1995 | (EP) . |
| 0707007A1 | 4/1996 | (EP) . |
| 757982 | 7/1996 | (EP) . |
| 540861 | 3/1985 | (ES) . |
| 2322161 | 8/1975 | (FR) . |
| 1109847 | 4/1968 | (GB) . |
| 62029558 | 2/1987 | (JP) . |
| 2286641 | 11/1990 | (JP) . |
| 90/13539 | 11/1990 | (WO) . |
| 94/26302 | 11/1994 | (WO) . |
| 95/01326 | 1/1995 | (WO) . |
| 96/31470 | 10/1996 | (WO) . |
| 96/31498 | 10/1996 | (WO) . |
| WO 96/31469 | 10/1996 | (WO) . |
| 96/39407 | 12/1996 | (WO) . |
| 96/40097 | 12/1996 | (WO) . |
| 97/09983 | 3/1997 | (WO) . |
| 97/11938 | 4/1997 | (WO) . |
| WO 97/44329 | 11/1997 | (WO) . |
| WO 98/04554 | 2/1998 | (WO) . |

OTHER PUBLICATIONS

CA: 121, No. 3 ; 35275n Sindelar et al, 1994.*
Chemical Abstract Accession No. 68:95436 (1980).
Šindelář, K. et al., "Potential Antidiarrheal Agents: 1–(11–Cyano–6,11–Dihydrodibenzo[b,e]Thiepin–10–Yl–Alkyl) and 1–(10–Cyano–10,11–Dihydrodibenzo[b,f]Thiepin–10–Yl–Alkyl)–4–Substituted Piperidines," *Collect Czechoslovak Chem. Commun.* 50:1089–1096 (1985).

(List continued on next page.)

*Primary Examiner*—Theodore J. Criares
(74) *Attorney, Agent, or Firm*—Hamilton, Brook, Smith & Reynolds, P.C.

(57) ABSTRACT

Disclosed is a method of treating a subject with a disease associated with aberrant leukocyte recruitment and/or activation. The method comprises administering to the subject a therapeutically effective amount of a compound represented by the following structural formula:

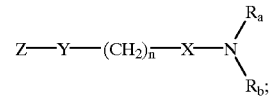

and physiologically acceptable salts thereof.

Z is a substituted or unsubstitured aromatic group.

Y is a covalent bond, —O— or —CO—.

n is an integer from one to about five.

X is a covalent bond or —CO—.

$R_a$ is an aliphatic or a substituted aliphatic group; $R_b$ is an aliphatic group substituted with an aromatic group or substituted aromatic group; and, taken together with the nitrogen atom bonded to $R_a$ and $R_b$, can form a substituted or unsubstituted non-aromatic heterocyclic ring.

36 Claims, 1 Drawing Sheet

OTHER PUBLICATIONS

Cervená, I., et al., "Potential Antidepressants: 2–(Aminoalkoxy)Biphenyls and Some Related ω–Substituted 2–Alkoxybiphenyls," *Collect Czech. Chem. Commun.*, 54:1966–1978 (1989).

Moerlein, S.M. and Stöcklin, G.L., "Synthesis of High Specific Activity [75Br]–and [77Br]Bromperidol and Tissue Distribution Studies in the Rat," *J. Med. Chem.* 28:1319–1324 (1985).

Hashizume, K., et al., "An Improved Purification Method for the Rapid Synthesis of High Purity Fluorobutyrophenone Neuroleptics from Nitro and Chloro Precursors Suitable for PET Study," *Chemistry Letters* pp:2295–2298 (1994).

Deshmukh, M.N., et al., "Titanium Mediated Cyclization of N–Substituted DI(β–Carbethoxyethyl)Amines: Preparation of 1–Substituted–3–Carbethoxy–4–Piperidones," *Synthethic Communications*, 25(2):177–182 (1995).

Midha, K.K., et al., "An Ultrasensitive Method for the Measurement of Haloperidol and Reduced Haloperidol in Plasma by High–Performance Liquid Chromatography with Coulometric Detection," *Therapeutic Drug Monitoring 10*: 177–183 (1988).

Taimr, L., et al., "New Spirobiindanetetrols from 3–Tert.Alkylpyrocatechols," *Tetrahedron Letters 34*:3707–3710 (1968).

Small, J.H., et al., "Synthesis and Characterization of Novel Spiro Penta–and Hexacoordinate Anionic Polysiliconate and Polygermylate Ionomers Derived from the Condensation of (±)5,5',6,6'–Tetrahydroxyl–1,1'–Spiro–Bis(Indane) with trialkoxysilanes, tetraalkoxysilanes, and trialkoxygermanes," *Polymer Mater Sci Eng 70*:378–379 (1993).

Munoz, A., et al., "Spirophosphoranes Macromoleculaires," *European Polymer Journal 15*:631–638 (1979). (Abstract).

Jancář, L., et al., "Spectrophotometric Study of Analytical Reactions of Triphenylmethane Dyes with Uranyl in the Presence of Cationic Surfactants," *Collection Czechoslovak Chem. Commun. 53*:1424–1460 (1988).

Tsubouchi, M., "Spectrophotometric Determination of Benzethonium with Tetrabromophenolphthalein Ethyl Ester," *Bulletin of the Chemical Society of Japan 44*:1560–1562 (1971).

Dallacker, F., et al., "Derivate des Benzo[1.3]dioxols, 44[1] Darstellung von p–chinoiden Brenzkatechinmethylenethern," *Z. Naturforsch 34b*:624–632 (1979). (Abstract).

Chapleo, C.B., et al., "α–Adrenoreceptor Reagents. 1. Synthesis of Some 1,4–Benzodioxans as Selective Presynaptic α$_2$–Adrenoreceptor Antagonists and Potential Antidepressants," *J. Med. Chem. 26*:823–831 (1983).

M.A. Davis, "New Psychotropic Agents, Analogs of Amitriptyline Containing the Normeperidine Group,", *J. Med. Chem.*, pp. 627–635 (Jul. 1967).

Belostotskaya, I.S., "3,6–Di–tert–butylpyrocatechol–based Cyclic Acetals," *Izv. Akad. Nauk, SSSR, Ser. Khim.* 12:2808–10 (1973).

Helwig, H. et al., Arzeni–mittel. Stuttgart: Helwig/Otto Arzenimittel, vol. 1, 8$^{th}$ edition, pp. 4–1 to 4–24. (1992).

\* cited by examiner

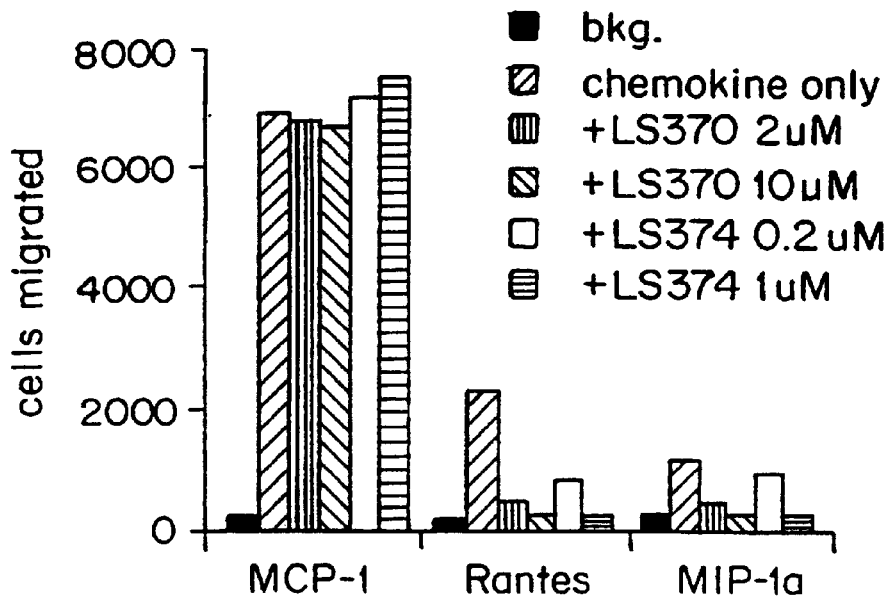
FIG. IA
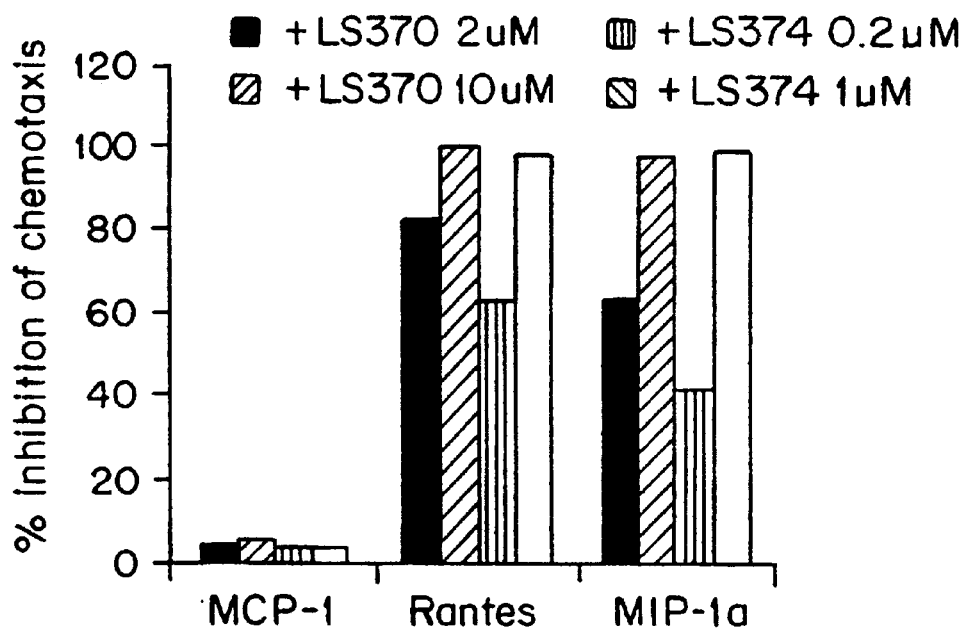
FIG. IB

CHEMOKINE RECEPTOR ANTAGONISTS AND METHODS OF USE THEREFOR

RELATED APPLICATIONS

This application claims priority to U.S. provisional application Serial No. 60/021,716, filed Jul. 12, 1996, the entire teachings of which are incorporated herein by reference.

BACKGROUND OF THE INVENTION

Chemoattractant cytokines or chemokines are a family of proinflammatory mediators that promote recruitment and activation of multiple lineages of leukocytes and lymphocytes. They can be released by many kinds of tissue cells after activation. Continuous release of chemokines at sites of inflammation mediates the ongoing migration of effector cells in chronic inflammation. The chemokines characterized to date are related in primary structure. They share four conserved cysteines, which form disulfide bonds. Based upon this conserved cysteine motif, the family is divided into two main branches, designated as the C—X—C chemokines (α-chemokines), and the C—C chemokines (β-chemokines), in which the first two conserved cysteines are separated by an intervening residue, or adjacent respectively (Baggiolini, M. and Dahinden, C. A., *Immunology Today*, 15:127–133 (1994)).

The C—X—C chemokines include a number of potent chemoattractants and activators of neutrophils, such as interleukin 8 (IL-8), PF4 and neutrophil-activating peptide-2 (NAP-2). The C—C chemokines include RANTES (Regulated on Activation, Normal T Expressed and Secreted), the macrophage inflammatory proteins 1α and 1β (MIP-1α and MIP-1β), and human monocyte chemotatic proteins 1–3 (MCP-1, MCP-2, MCP-3), which have been characterized as chemoattractants and activators of mcnocytes or lymphocytes but do not appear to be chemoattractants for neutrophils. Chemokines, such as RANTES and MIP-1α, have been implicated in a wide range of human acute and chronic inflammatory diseases including respiratory diseases, such as asthma and allergic disorders.

The chemokine receptors are members of a superfamily of G protein-coupled receptors (GPCR) which share structural features that reflect a common mechanism of action of signal transduction (Gerard, C. and Gerard, N. P., *Annu Rev. Immunol.*, 12:775–808 (1994); Gerard, C. and Gerard, N. P., *Curr. Opin. Immunol.*, 6:140–145 (1994)). Conserved features include seven hydrophobic domains spanning the plasma membrane, which eLre connected by hydrophilic extracellular and intracebllular loops. The majority of the primary sequence homology occurs in the hydrophobic transmembrane regions with the hydrophilic regions being more diverse. The first receptor for the C—C chemokines that was cloned and expressed binds the chemokines MIP-1α and RANTES. Accordingly, this MIP-1α/RANTES receptor was designated C—C chemokine receptor 1 (also referred to as CCR-1; Neote, K., et al., *Cell*, 72:415–425 (1993); Horuk, R. et al., WO 94/11504, May 26, 1994; Gao, J.-I. et al., *J. Exp. Med.*, 177:1421–1427 (1993)). Three new receptors have been characterized which bind and/or signal in response to RANTES: CCR3 mediates binding and signaling of chemokines including eotaxin, RANTES, and MCP-3 (Ponath et al., *J. Exp. Med.*, 183:2437 (1996)), CCR4 binds chemokines including RANTES, MIP-1α, and MCP-1 (Power, et al., *J. Biol. Chem.*, 270:19495 (1995)), and CCR5 binds chemokines including MIP-1α, RANTES, and MIP-1β (Samson, et al., *Biochem.* 35: 3362–3367 (1996)). RANTES is a chemotactic chemokine for a variety of cell types, including monocytes, eosinophils, and a subset of T-cells. The responses of these different cells may not all be mediated by the same receptor, and it is possible that the receptors CCR1, CCR4 and CCR5 will show some selectivity in receptor distribution and function between leukocyte types, as has already been shown for CCR3 (Ponath et al.). In particular, the ability of RANTES to induce the directed migration of monocytes and a memory population of circulating T-cells (Schall, T. et al., *Nature*, 347:669–71 (1990)) suggests this chemokine and its receptor(s) may play a critical role in chronic inflammatory diseases, since these diseases are characterized by destructive infiltrates of T cells and monocytes.

Many existing drugs have been developed as antagonists of the receptors for biogenic amines, for example, as antagonists of the dopamine and histamine receptors. No successful antagonists have yet been developed to the receptors for the larger proteins such as chemokines and C5a. Small molecule antagonists of he interaction between C—C chemokine receptors and their ligands, including RANTES and MIP-1α, would provide compounds useful for inhibiting harmful inflammatory processes "triggered" by receptor ligand interaction, as well as valuable tools for the investigation of receptor-ligand interactions.

SUMMARY OF THE INVENTION

It has now been found that a number of small organic molecules are antagonists of chemokine receptor function and can inhibit leukocyte activation and/or recruitment. An antagonist of chemokine receptor function is a molecule which can inhibit the binding of one or more chemokines, including C—C chemokines such as RANTES and MIP-1α, to one or more chemokine receptors on leukocytes and/or other cell types. As a consequence, processes and cellular responses mediated by chemokine receptors can be inhibited with these small organic molecules. Based on this discovery, a method of treating a subject with a disease associated with aberrant leukocyte recruitment and/or activation is disclosed. The method comprises administering to the subject a therapeutically effective amount of a compound or small organic molecule which is an antagonist of chemokine receptor function. Compounds or small organic molecules which have been identified as antagonists of chemokine receptor function are discussed in detail hereinbelow, and can be used for the manufacture of a medicament for treating or for preventing a disease associated with aberrant leukocyte recruitment and/or activation. The invention also relates to the disclosed compounds and small organic molecules and their use in treating or preventing a disease associated with aberrant leukocytes recruitment and/or activation. The invention also includes pharmaceutical compositions comprising one or more of the compounds or small organic molecules which have been identified herein as antagonists of chemokine function and a suitable pharmaceutical carrier. The invention further relates to novel compounds which can be used to treat an individual with a disease associated with aberrant leukocyte recruitment and/or activation.

BRIEF DESCRIPTION OF THE FIGURES

FIG. 1A and FIG. 1B are histograms illustrating the inhibition by varying concentrations of LS370 and LS374 (also referred to herein as "L-370" and "L-374", respectively) in the chemotaxis of fresh peripheral blood mononuclear cells (PBMC) in response to RANTES or MIP-1α.

DETAILED DESCRIPTION OF THE INVENTION

The present invention relates to small molecule compounds which are antagonists of chemokine receptor function. Accordingly, processes or cellular responses mediated by the binding of a chemokine to a receptor can be inhibited (reduced or prevented, in whole or in part), including leukocyte migration, integrin activation, transient increases in the concentration of intracellular free calcium $[Ca^{++}]_i$, and/or granule release of proinflammatory mediators.

The invention further relates to a method of treatment, including prophylactic and therapeutic treatments, of a disease associated with aberrant leukocyte recruitment and/or activation, including chronic inflammatory disorders characterized by the presence of RANTES and/or MIP-1α responsive T cels, monocytes and/or eosinophils, including but not limited to diseases such as arthritis, psoriasis, multiple sclerosis, inflammatory bowel diseases such as ulcerative colitis and Crohn's disease, as well as allergies and asthma. Other diseases associated with aberrant leukocyte recruitment and/or activation which can be treated (including prophylactic treatments) with the methods disclosesd herein are inflammatory diseases associated with Human Immunodeficiency Virus (HIV) infection, e.g., AIDS associated encephalitis, AIDS related maculopapular skin eruption, AIDS related interstitial pneumonia, AIDS related enteropathy, AIDS related periportal hepatic inflammation and AIDS related glomerulo nephritis. The method comprises administering to a subject a therapeutically effective amount of a compound (i.e., one or more compounds) which inhibits chemokine receptor function, inhibits the binding of a chemokine to leukocytes and/or other cell types, and/or which inhibits leukocyte migration to, and/or activation at, sites of inflammation. According to the method, chemokine-mediated chemotaxis and/or activation of pro-inflammatory cells bearing receptors for chemokines can be inhibited. As used herein, "pro-inflammatory cells" includes but is not limited to leukocytes, since chemokine receptors may be expressed on other cell types, such as neurons and epithelial cells.

In one embodiment of the present invention, the antagonist of chemokine receptor function is represented by Structural Formula (I):

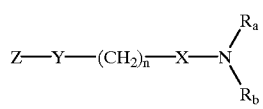

(I)

Z is a substituted or unsubstituted aromatic group.

Y is a covalent bond, —O— or —CO—.

n is an integer from one to about five. n is preferably one, two, or three.

X is a covalent bond or —CO—.

$R_a$ and $R_b$, taken together with the nitrogen atom to which they are bonded, form a substituted or unsubstituted non-aromatic heterocyclic ring. For example, $R_a$ and $R_b$, together with the nitrogen atom to which they are bonded, form a four, five, six, seven or eight-membered nitrogen-containing non-aromatic ring. Alternatively $R_a$ is an aliphatic or a substituted aliphatic group and $R_b$ is an aliphatic group substituted with an aromatic group or substituted aromatic group.

In a preferred embodiment, $R_a$ and $R_b$, together with the nitrogen atom to which they are bonded, form a six-membered nitrogen-containing non-aromatic ring. For example, the six-membered, nitrogen-containing non-aromatic ring can be chosen such that the antagonist of chemokine receptor function is represented by Structural Formula (II):

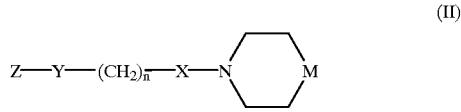

(II)

Z, Y, X and n are as described in Structural Formula (I).

M is >NR$_2$, >CR$_1$R$_2$, —O—, —S— or —CO—. M is preferably >NR$_2$ or >CR$_1$R$_2$.

R$_1$ is —H, —OH, an aliphatic group, —O-(aliphatic group), —SH or —S-(aliphatic group). Preferably, R$_1$ is —H or —OH.

R$_2$ is an aliphatic group, a substituted aliphatic group, an aromatic group, a substituted aromatic group, a benzylic group, a substituted benzylic group, a non-aromatic heterocyclic group or a substituted non-aromatic heterocyclic group.

When M is >NR$_2$ or >CR$_1$R$_2$, the antagonist of chemokine receptor function is preferably a compound represented by Structural Formulas (III) through (VIII):

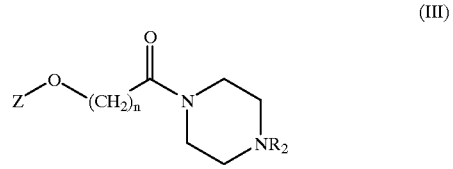

(III)

(IV)

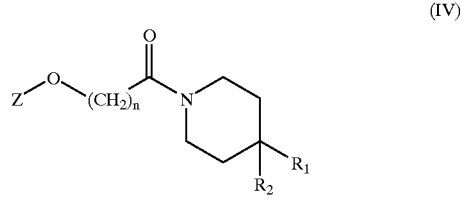

(V)

(VI)

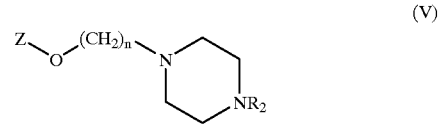

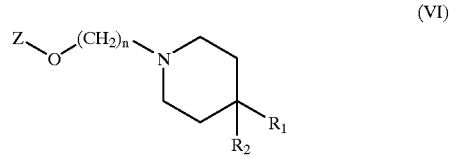

(VII)

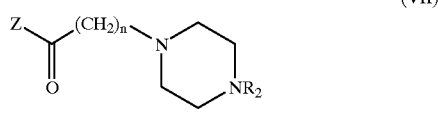

(VIII)

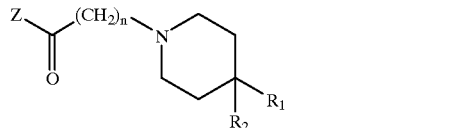

In Structural Formulas (III) and (IV), n is preferably one, two or three, more preferably one. When n is one and R$_1$ is —H or —OH, R$_2$ is preferably a C$_1$ to about a C$_4$ alkyl group substituted with an aromatic or substituted aromatic group.

In Structural Formulas (V) and (VI), n is preferably one, two or three, more preferably two or three. When n is two or three and $R_1$ is —H or —OH, $R_2$ is preferably an aliphatic or substituted aliphatic group, preferably an alkyl group substituted with a hydroxyl, alkoxy, thiol, or alkylthiol group.

In Structural Formulas (VII) and (VIII), n is preferably one, two or three, more preferably three. When n is three and $R_1$ is —H or —OH, $R_2$ is preferably an aromatic group, a substituted aromatic group or an aliphatic group substituted with an aromatic or substituted aromatic group.

In another preferred embodiment, —X— and —Y— in Structural Formula (II) are each a covalent bond and the antagonist of chemokine receptor function is a compound represented by Structural Formula (IX):

(IX)

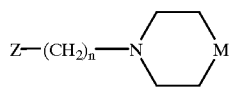

Z, n and M are as described above for Structural Formula (II). Preferably, Z is a tricyclic ring system comprising two carbocyclic aromatic groups fused to a seven or eight membered cycloalkyl group or to a non-aromatic heterocyclic ring. In one example, Z is represented by Structural Formula (IXa):

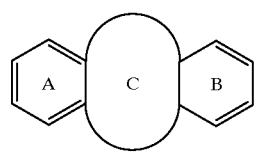

The phenyl rings in Structural Formula (IXa), labeled with an "A" and "B", are referred to herein as "Ring A" and "Ring B", respectively. The central ring, labeled with a "C", is referred to as "Ring C" and can be, for example a seven or eight membered non-aromatic carbocyclic ring (e.g., a cycloheptane or cyclooctane ring) or a non-aromatic heterocyclic ring. When Ring C is a non-aromatic heterocyclic ring, it can contain one or two heteroatoms such as nitrogen, sulfur or oxygen. When Z is represented by Structural Formula (IXa), the tricyclic ring system is connected to the alkylene group in Structural Formula (IX) by a single covalent bond between the alkylene group and a ring atom in Ring C which is not also in Ring A or Ring B.

Ring A and/or Ring B can be unsubstituted. Alternatively, Ring A and/or Ring B can have one or more substituents. Suitable substituents are as described hereinbelow for substituted aromatic groups.

In addition, Ring C optionally contains one or more additional substituents, for example, $R_3$ and $R_4$. When Ring C is a non-aromatic carbocyclic ring, substituents such as $R_3$ and $R_4$ are as described hereinbelow for substituted aliphatic rings. When Ring C contains one or more heteroatoms, substituents such as $R_3$ and $R_4$ are as described below for non-aromatic heterocyclic rings. Preferably, $R_3$ is —H and $R_4$ is —H or an electron withdrawing group. Suitable electron withdrawing groups include —CN, alkylsulfonyl, carboxamido, carboxylic alkyl esters, —$NO_2$ and halogens (e.g., —Br and —Cl).

More preferably, Z in Structural Formula (IX) is represented by Structural Formulas (X) and (XI):

(X)

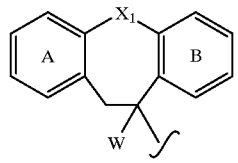

(XI)

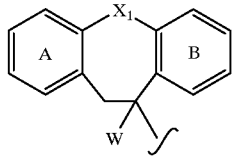

$X_1$ is a chemical bond, —S—, —$CH_2$— or —$CH_2S$—. Preferably, $X_1$ is —S— in Structural Formula (X) and —$CH_2S$— in Structural Formula (XI).

W is —H or an electron withdrawing group, as described above for Structural Formula (IXa). A preferred electron withdrawing group is —CN. Ring A and Ring B are as described above in Structural Formula (IXa).

When $X_1$ in Structural Formula (X) is —S— or when $X_1$ in Structural Formula (XI) is —$CH_2S$—, M is preferably >$NR_2$ or >$CR_1R_2$. When M is >$NR_2$ or >$CR_1R_2$, W is preferably —CN and n is preferably two, three or four, more preferably three. $R_1$ is preferably —H or —OH.

In another preferred embodiment, $R_a$ is an aliphatic or a substituted aliphatic group and $R_b$ is an aliphatic group substituted with an aromatic group or substituted aromatic group. As a consequence, the antagonist of chemokine receptor function is a compound represented by Structural Formula (XII):

(XII)

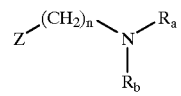

Preferably, n is an integer from about two to about four; $R_a$ is a $C_1$ to about a $C_4$ substituted or unsubstituted alkyl group; and $R_b$ is —$(CH_2)_m$—$R_{10}$, wherein m is an integer from about two to about four, and $R_{10}$ is an aromatic group.

In yet another preferred embodiment, the antagonist of chemokine function is a compound represented by Structural Formula (I), wherein Z is represented by Structural Formulas (X) or (XI) and —X— and —X— are each a covalent bond. In this instance the antagonist of chemokine receptor function is a compound represented by Structural Formulas (XIII) or (XIV):

(XIII)

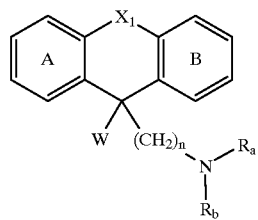

-continued (XIV)

In Structural Formulas (XIII) and (XIV), $X_1$, is as defined above for Structural Formulas (X) and (XI); n is an integer from two to five; W is —H, —CN, alkylsulfonyl, carboxamido or carboxyalkyl;

In Structural Formulas (XIII) anci (XIV), Ring A is substituted with $R_8$ and $R_9$, wherein $R_8$ and $R_9$ are independently —H, a halogen, alkoxy or alkyl, or, taken together with ring A, form a naphthyl group; and $R_a$ and $R_b$ are independently —H, alkyl, aralkyl or, taken together with the nitrogen atom bonded to $R_a$ and $R_b$, form a non-aromatic heterocyclic ring represented by a structure selected from:

$R_5$ is —H, alkanoyl, aroyl, aralkoyl, alkyl, aralkyl or cycloalkanoyl.

$R_6$ is an aryl group.

$R_7$ is —H or a heterocylic ring.

In another embodiment of the present invention, the antagonist of chemokine receptor function is represented by Structural Formula (XVI):

(XVI)

A is >$NR_{14}$, —O—, —S—, —$CH_2$—, —$CH(R_{14})$— or —C ($R_{14}R_{15}$)—.

$R_{11}$ is —H, halogen, —CN, an aliphatic group, a substituted aliphatic group, an aromatic group, a substituted aromatic group, —OH, —O-(aliphatic group), —O-(substituted aliphatic group), —S-(aliphatic group), —S-(substituted aliphatic group), —$NO_2$, —$NH_2$, —NH(aliphatic group), —NH(substituted aliphatic group), —N(aliphatic group)$_2$, —N(substituted aliphatic group)$_2$.

$R_{12}$ is an aromatic group or an aliphatic group.

Each $R_{13}$ is independently chosen and is —H, an aliphatic group or substituted aliphatic group. Thus, if n is greater than one, the $R_{13}$ attached to one double bond can be the same as or different from the $R_{13}$ substituents attached to the other double bonds. Structural Formula (XVI) indicates that each $R_{13}$ can be bonded to either carbon atom in the double bond and that the stereochemistry of each double bond is independently selected and can be cis or trans.

n is an integer from one to about four.

B is —N($R_{16}$)—, —S—, —O— or a covalent bond.

$R_{14}$, $R_{15}$ and $R_{16}$ are independently an aliphatic group or a substituted aliphatic group and can be the same or different.

Q is an aliphatic group, a substituted aliphatic group, a benzylic group, a substituted benzylic group, an aromatic group, a substituted aromatic group, a non-aromatic heterocyclic group or a substituted non-aromatic heterocyclic group.

In a preferred embodiment, n is 1 and B and Q are as defined above. In this instance, A is preferably —O—, —S— or >C($CH_3$)$_2$; B is —N($R_{16}$)—, —S— or a covalent bond and $R_{13}$ is preferably —H or, when B is —S—, an aliphatic or substituted aliphatic group bonded to the same olefinic carbon atom as sulfur. As a consequence, the antagonist of chemokine receptor function is a compound represented by one of Structural Formulas (XVII) through (XXV):

(XVII)

(XVIII)

(XIX)

(XX)

-continued

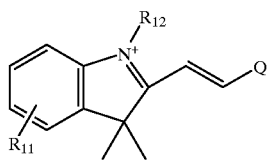
(XXI)

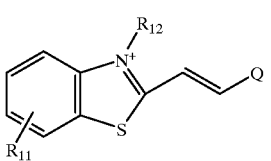
(XXII)

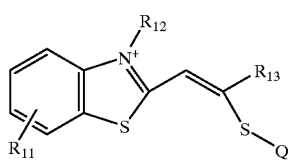
(XXIII)

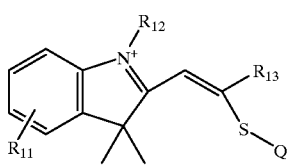
(XXIV)

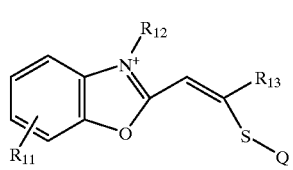
(XXV)

In Structures (XVII) through (XXV), $R_{13}$ and $R_{16}$ are preferably an aliphatic group.

Alternatively, in Structural Formula XVI, B, Q and the terminal olefin carbon, taken together, form a non-aromatic heterocyclic ring. The antagonist of chemokine receptor function is then represented by Structural Formula (XXVI):

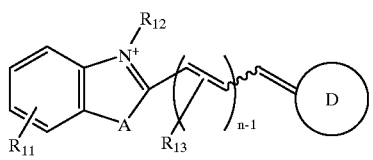
(XXVI)

$R_{11}$, $R_{12}$, $R_{13}$ and n are as described above for Structural Formula (XVI). Optionally, the non-aromatic heterocyclic ring in Structural Formula (XXVI), designated with a "D" and referred to herein as "Ring D", can be fused to an aromatic ring or substituted aromatic ring. The non-aromatic heterocyclic ring can be substituted or unsubstituted. In one example, Ring D is represented by the following structural formula:

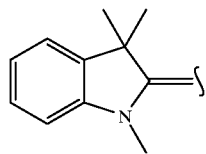

In another embodiment of the present invention, the antagonist of chemokine receptor function is represented by Structural Formula (XXVII):

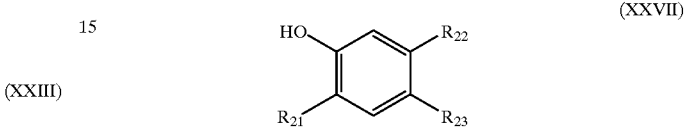
(XXVII)

$R_{21}$ is —OH, an aliphatic group, a substituted aliphatic group, —O-(aliphatic group), —O-(substituted aliphatic group), —O—CO-(aliphatic group) or —O—CO-(substituted aliphatic group). Preferably, $R_{21}$ is —OH, $CH_3CO$—O— or an alkyl group substituted with $CH_3NH$- (e.g., an alkyl group substituted at the benzylic carbon atom with methylamino methylene). Examples of $R_{21}$ include —OH, $CH_3CO$—O— or —CH (—CH($CH_3$)$_2$)(—$CH_2NHCH_3$).

$R_{22}$ and $R_{23}$ are independently —H, an aliphatic group, a substituted aliphatic group, an aromatic group, a substituted aromatic group, —S-(aliphatic group), —S-(substituted aliphatic group), —O-(aliphatic group), —O-(substituted aliphatic group), —(CH$_2$)$_n$—R$_{26}$, and, taken together, can be a —(CH$_2$)— to —(CH$_2$)$_5$— alkylene group or a —(CH$_2$)$_2$— to —(CH$_2$)$_5$— alkylene group substituted with one or more aliphatic groups, substituted aliphatic groups, aromatic groups or substituted aromatic groups. Preferably, $R_{22}$ is thioalkyl, alkyl or phenyl and $R_{23}$ is —H, methyl or, taken together with $R_{22}$, a propylene group. The propylene group can be unsubstituted or substituted with one or more methyl or ethyl groups. Examples of $R_{22}$ include —$SC_7H_{15}$, methyl or phenyl. Examples of $R_{23}$ include —H, methyl or, taken together with $R_{22}$, a —$CH_2CH_2C(CH_3)_2$-group.

$R_{26}$ is a substituted or unsubstituted aromatic group.

In one aspect, the antagonist of chemokine receptor function is a compound represented by Structural Formula (XXVII), wherein:

$R_{21}$ is —OH, an alkyl group, an alkoxy group, an acetoxy group or an alkyl group substituted with —$NR_{24}R_{25}$;

$R_{22}$ and $R_{23}$ are independently an alkyl group, an aromatic group, an aralkyl group, and ethylene-$R_6$ or thioalkyl, and, taken together, form an alkylene group;

$R_{24}$ and $R_{25}$ are independently an alkyl group, an aralkyl group and an aryl group;

$R_{26}$ is a phenyl group substituted by $R_{27}$ and $R_{28}$; and $R_{27}$ and $R_{28}$ are independently —H, —OH, alkoxy, or halogen.

In another embodiment of the present invention, the antagonist of chemokine function is a compound represented by Structural Formula (XXVIII):

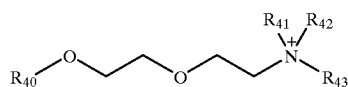

(XXVIII)

$R_{40}$ and $R_{43}$ are independently an aliphatic group, a substituted aliphatic group, a benzyic group, a substituted benzylic group, an aromatic group, a substituted aromatic group, a non-aromatic heterocyclic group or a substituted non-aromatic heterocyclic group.

$R_{41}$ and $R_{42}$ are independently an aliphatic group or a substituted aliphatic group. Preferably, $R_{41}$ and $R_{42}$ are each a methyl group.

In another embodiment of the present invention, the antagonist of chemokine receptor function is a compound represented by Structural Formula (XXIX):

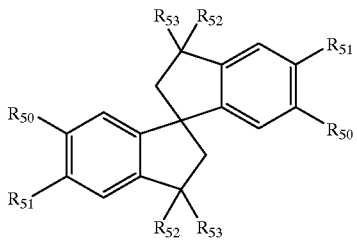

(XXIX)

$R_{50}$ and $R_{51}$ are independently —OH, a halogen, —O-(aliphatic group), —O-(substituted aliphatic group), —O—CO-(aliphatic group), —O—CO-(substituted aliphatic group), —NH$_2$, —NH(aliphatic group), —NH(substituted aliphatic group), —N(aliphatic group)$_2$, —N(substituted aliphatic group)$_2$, —S-(aliphatic group) or —S-(substituted aliphatic group). Preferably, $R_{50}$ and $R_{51}$ are independently —OH, a halogen, —O-(aliphatic group) or —O-(substituted aliphatic group).

$R_{52}$ and $R_{53}$ are independently —H, an aliphatic group, a substituted aliphatic group, a halogen, —NH$_2$, —NH(aliphatic group), —NH(substituted aliphatic group), —N(aliphatic group), or —N(substituted aliphatic group)$_2$. Preferably, $R_{52}$ and $R_{53}$ are independently an aliphatic group, a substituted aliphatic group or a halogen.

Also included in the present invention are physiologically acceptable salts of he compounds represented by Structural Formulas (I) through (XXIX). Salts of compounds containing an amine or other basic group can be obtained, for example, by reacting with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like.

As used herein, aliphatic groups include straight chained, branched or cyclic $C_1$-$C_8$ hydrocarbons which are completely saturated or which contain one or more units of unsaturation.

An "alkyl group" is a saturated aliphatic group, as defined above. The term "alkoxy" refers to an alkyl ether chain with an alkyl group. "Alkanoyl" refers to alkyl substituted carbonyl; "aralkanoyl" refers to phenyl-alkyl-CO— and "aroyl" refers to arylcarbonyl including benzoyl, naphthoyl and the like. The term "halogen" means fluoro, chloro, bromo and iodo. The term "aryl", as opposed to the term "aromatic group", means phenyl. The term "substituted phenyl" means aryl substituted by alkyl, halogen, alkoxy, nitro, amino, acetamido, cyano and trifluoromethyl and naphthyl. "Aralkyl" means —(CH$_2$)$_x$-phenyl, wherein x is an integer from one to four including benzyl. It is noted that the terms "aromatic group", "carbocylic aromatic group" and "heterocyclic aromatic group" are defined below and have different meanings from the term "aryl".

Aromatic groups include carbocycLic aromatic groups such as phenyl, 1-naphthyl, 2-naphthyl, 1-anthracyl and 2-anthacyl, and heterocyclic aromatic groups such as N-imidazolyl, 2-imidazole, 2-thienyl, 3-thienyl, 2-furanyl, 3-furanyl, 2-pyridyl, 3-pyridyl, 4-pyridyl, 2-pyrimidy, 4-pyrimidyl, 2-pyranyl, 3-pyranyl, 3-pyrazolyl, 4-pyrazolyl, 5-pyrazolyl, 2-pyrazinyl, 2-thiazole, 4-thiazole, 5-thiazole, 2-oxazolyl, 4-oxazolyl and 5-oxazolyl.

Aromatic groups also include fused polycyclic aromatic ring systems in which a carbocyclic aromatic ring or heteroaryl ring is fused to one or more other heteroaryl rings. Examples include 2-benzothienyl, 3-benzothienyl, 2-benzofuranyl, 3-benzofuranyl, 2-indolyl, 3-indolyl, 2-quinolinyl, 3-quinolinyl, 2-benzothiazole, 2-benzooxazole, 2-benzimidazole, 2-quinolinyl, 3-quinolinyl, 1-isoquinolinyl, 3-quinolinyl, 1-isoindolyl, 3-isoindolyl, and acridintyl. Also included within the scope of the term "aromatic group", as it is used herein, is a group in which one or more carbocyclic aromatic rings and/or heteroaromatic rings are fused to a cycloalkyl or non-aromatic heterocyclic ring. Examples include decalin, phthalimido, benzodiazepines, benzooxazepines, benzooxazines, phenothiazines, and groups represented by the following structural formulas:

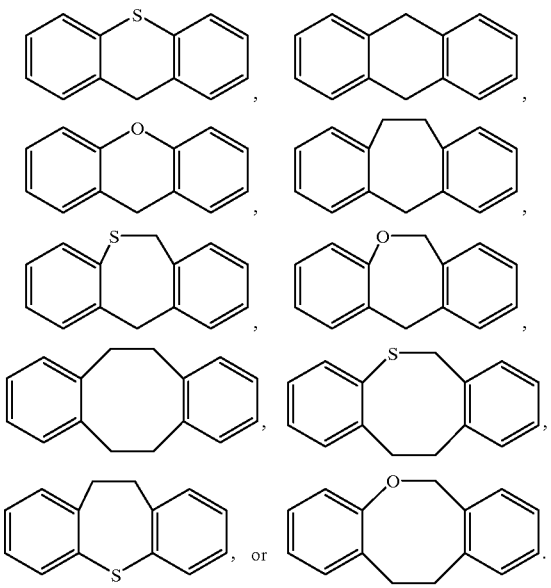

Non-aromatic heterocyclic rings are non-aromatic carbocyclic rings which include one or more heteroatoms such as nitrogen, oxygen or sulfur in the ring. The ring can be five, six, seven or eight-membered. Examples include 2-tetrahydrofuranyl, 3-tetrahydrofuranyl, 2-tetrahyrothiophenyl, 3-tetrahyrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl and 4-thiazolidinyl.

"Heterocyclic ring", as opposed to "heteroaryl group" and "non-aromatic heterocylic ring", is defined as imidazole, benzimidazole, pyridine, pyrimidine, thiazole, benzothiazole, thienyl, benzothienyl. It is noted further the terms "heterocyclic aromatic group" and "non-aromatic heterocyclic ring" are defined above and have different meanings from the term "heterocyclic ring".

Suitable substituents on an alkyl, aliphatic, aromatic, non-aromatic heterocyclic ring or benzyl group include, for example, —OH, halogen (—Br, —Cl, —I and —F) —O(aliphatic, substituted aliphatic, benzyl, substituted benzyl, aromatic or substituted aromatic group), —CN, —NO, —COOH, —NH$_2$, —NH(aliphatic group, substituted aliphatic, benzyl, substituted benzyl, aromatic or substituted aromatic group), —N(aliphatic group, substituted aliphatic, benzyl, substituted benzyl, aromatic or substituted aromatic group)$_2$, —COO(aliphatic group, substituted aliphatic, benzyl, substituted benzyl, aromatic or substituted aromatic group), —CONH$_2$, —CONH(aliphatic, substituted aliphatic group, benzyl, substituted benzyl, aromatic or substituted aromatic group)), —SH, —S(aliphatic, substituted aliphatic, benzyl, substituted benzyl, aromatic or substituted aromatic group) and —NH—C(=NH)—NH$_2$. A substituted non-aromatic heterocyclic ring, benzylic group or aromatic group can also have an aliphatic or substituted aliphatic group as a substituent. A substituted alkyl or aliphatic group can also have a non-aromatic heterocyclic ring, benzyl, substituted benzyl, aromatic or substituted aromatic group as a substituent. A substituted non-aromatic heterocyclic ring can also have =O, =S, =NH or =N(aliphatic, aromatic or substituted aromatic group) as a substituent. A substituted aliphatic, substituted aromatic, substituted non-aromatic heterocyclic ring or substituted benzyl group can have more than one substituent.

In the structural formulas depicted herein, the single or double bond by which a chemical group or moiety is connected to the remainder of the molecule or compound is indicated by the following symbol:

For example, the corresponding symbol in Structural Formula (X) or (XI) indicates that the tricyclic ring system, which respresents Z in Structural Formula (IX), is connected to the alkylene group in Structural Formula (IX) by a single covalent bond between the alkylene group and the ring carbon in Ring C which is bonded to W.

A "subject" is preferably a mammal, such as a human, but can also be an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like).

A "therapeutically effective amount" of a compound is an amount which results in the inhibition of one or more processes mediated by the binding of a chemokine to a receptor in a subject with a disease associated with aberrant leukocyte recruitment and/or activation. Examples of such processes include leukocyte migration, integrin activation, transient increases in the concentration of intracellular free calcium $[Ca^{2+}]_i$ and granule release of proinflammatory mediators. Alternatively, a "therapeutically effective amount" of a compound is a quantity sufficient to achieve a desired therapeutic and/or prophylactic effect, such as an amount which results in the prevention of or a decrease in the symptoms associated with a disease associated with aberrant leukocyte recruitment and/or activation.

The amount of compound administered to the individual will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. Typically, a therapeutically effective amount of the compound can range from about 0.1 mg per day to about 100 mg per day for an adult. Preferably, the dosage ranges from about 1 mg per day to about 100 mg per day. An antagonist of chemokine receptor function can also be administered in combination with one or more additional therapeutic agents, e.g. theophylline, β-adrenergic bronchdilators, corticosteroids, antihistamines, antiallergic agents and the like.

The compound can be administered by any suitable route, including, for example, orally in capsules, suspensions or tablets or by parenteral administration. Parenteral administration can include, for example, systemic administration, such as by intramuscular, intravenous, subcutaneous, or intraperitoneal injection. The compound can also be administered orally (e.g., dietary), topically, by inhalation (e.g., intrabronchial, intranasal, oral inhalation or intranasal drops), or rectally, depending on the disease or condition to be treated. Oral or parenteral administration are preferred modes of administration.

The compound can be administered to the individual in conjunction with an acceptable pharmaceutical carrier as part of a pharmaceutical composition for treatment of HIV infection, inflammatory disease, or the other diseases discussed above. Formulation of a compound to be administered will vary according to the route of administration selected (e.g., solution, emulsion, capsule). Suitable pharmaceutical carriers may contain inert ingredients which do not interact with the compound. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

The activity of compounds of the present invention can be assessed using suitable assays, such as receptor binding assays and chemotaxis assays. For example, as described in Exemplification Section, small molecule antagonists of RANTES and MIP-1α binding have been identified utilizing HL-60 (butyric acid differentiated) cells which bind RANTES and chemotax in response to RANTES and MIP-1α as a model for leukocyte chemotaxis. Specifically, a high through-put receptor binding assay, which monitors $^{125}$I-RANTES and $^{125}$I-MIP-1α binding to HL-60 cell membranes, was used to identify small molecule antagonists which block binding and RANTES and MIP-1α mediated HL-60, T-cell, peripheral blood mononuclear cell, and eosinophil cheaiotactic response. Compounds of the present invention can also be identified by virtue of their ability to inhibit the activation steps triggered by binding of a chemokine to its receptor, such as chemotaxis, integrin activation and/or granule mediator release.

The compounds represented by Structural Formula (IX), wherein Z is represented by Structural Formulas (IXa), (X) and (XI) and compounds represented by Structural Formulas (XIII) and (XIV) can be prepared according to methods described in *Collect. Czech. Chem. Commun.*, 50(5): 1089–96 (1985) (CA 104:33990) and Czech Patent CS 240698 B1 870601 (CA 109:92794). The teachings of these references and references cited therein are incorporated herein by reference. For example, these compounds can be prepared by the following reaction scheme:

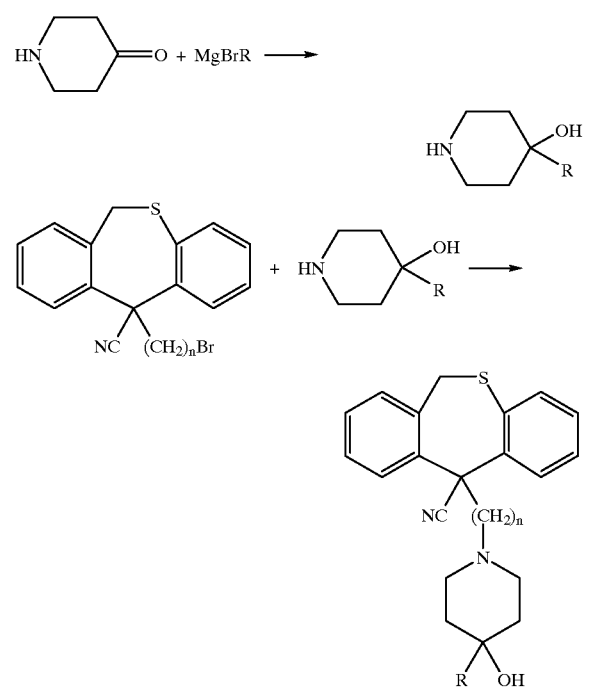

Compounds represented by Structural Formula (V) and (VI), for example, the compounds designated in Table 1 as L-380 and Table 2 as L-372, can be prepared according to methods described in *Collect. Czech. Chem. Commun.*, 54(7):1966–1978 (1989), Czech Patent CS-268400 (1991) and WO 90/13539, the teachings of which are incorporated herein by reference.

Compounds represented by Structural Formula (VII) and (VIII), for example, the compound designated as L-348 in Table 2, can be prepared according to methods described in *Synth. Commun.* 25(2): 177–82 (1995), *Chem. Lett.*, (12): 2295–8 (1994), *Ther. Drug. Monit.* 10(2): 177–83 (1988), *J. Med. Chem.* 28(9): 1319–24 (1985), U.S. Pat. No. 4,086,234, U.S. Pat. No. 4,012,514, U.S. Pat. No. 3,936,468, U.S. Pat. No. 3,922,266 and U.S. Pat. No. 3,907,812, the teachings of which are incorporated herein by reference.

Compounds represented by Structural Formula (III) and (IV), for example the compound designates as L-377 in Table 2, can be prepared according to methods well known in the field of organic chemistry, for example, by reacting the sodium salt of a suitable phenol and a suitable alkylating agent. The phenol is preferably substituted with electron withdrawing groups (e.g., 3,4,5-trimesthoxyphenol). This reaction is shown schematically below:

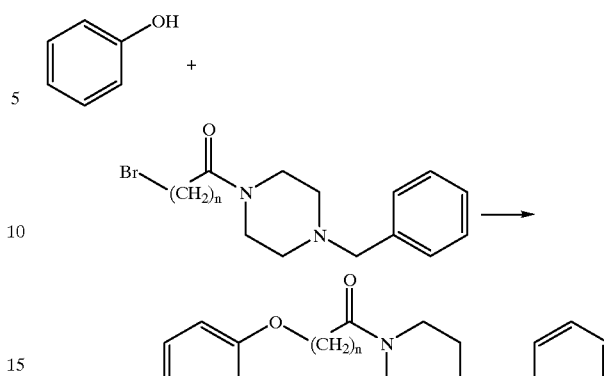

The phenol in the scheme above is preferably substituted with one or more electron withdrawing groups. The alkylating agent prepared, for example, by reacting a suitable bromo substituted acyl bromide (e.g., bromoacetyl bromide) with a suitable 1-substituted piperazine, for example, 1-benzylpiperazine, as shown below:

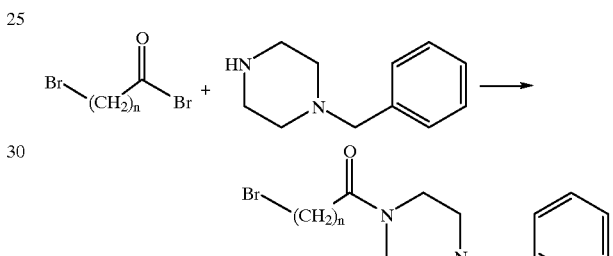

Compounds represented by Structural Formula (XII), for example, the compound designated L-347 in Table 1, can be prepared according to methods described in WO 97/11938, WO 97/09983, WO 96/40097, WO 96/39407 and EP 694543, the teachings of which are incorporated herein by reference.

Compounds represented by Structural Formula (XVIII) and (XXI), for example the compound designated L-344 in Table 2, can be prepared, for example, by reacting a 1,3,3-trialkylindolinium anion with a suitable alkylating agent according to methods described in European Patent 94 EP 0400348 and U.S. Pat. No. 5,258,274, the teachings of which are incorporated herein by reference. By replacing the 1,3,3-trialkylindolinium anion with an appropriate 1-alkyl-benzoxazolinium anion or 1-alkyl-benzothiazolinium anion, similar procedures can be used to prepare compound represented by Structural Formulas (XVII), (XIX), (XX) and (XXII) through (XXV) (e.g., compounds designated as L-459 and L-464 in Table II). These procedures are also suitable for preparing compounds represented by Structural Formula (XXVI), for example, the compound designated L-342 in Table 2, by using an appropriate alkylating agent.

Compounds represented by Structural Formula (XXVII), for example, the compound designated L-381 in Table 1, can be prepared according to methods described in EP 757982, EP 533056, EP 457701, EP 434093 and EP 332064, the teachings of which are incorporated herein by reference. Other compounds represented by Structural Formula (XXVII), for example, the compound designated L-345 in Table 1, can be prepared according to methods described in *Sb. Pr. Vyzk. Chem. Vyuziti Uhli, Dehtu Ropy* 7:21–39

(1967), Z. Naturforsch. B: *Anorg. Chem. Org. Chem* 34B (4):624–32 (1979) and *J. Med. Chem*. 26(6): 823–31 (1983), the teachings of which are incorporated herein by reference. Yet other compounds represented by Structural Formula (XXVII), for example, the compound designated L-349 in Table 1, can be prepared according to methods described in EP 707007, WO 9501326, EP596692, EP 587050, EP 540165 and CA 2028031, the teachings of which are incorporated herein by reference.

Compounds represented by Structural Formula (XXVIII), for example, the compound designated L-339 in Table 1, can be prepared according to methods described in WO 94/26302, *Collect. Czech. Chem. Commun*. 53(7):1424–60 (1988), EP 226448, ES 540861 and *Bull. Chem. Soc. Jap* 44(6):1560–2, the teachings of which are incorporated herein by reference.

Compounds represented by Structural Formula (XXIX), for example, the compound designated L-319 in Table 1, can be prepared according to methods described in JP 09110771, *Polym. Mater. Sci. Eng*. 70:378–9 (1993), JP 03148232, JP 02286642, JP 03386641, JP 02248954, EP 342035, EP 307951, *Eur. Polym. J*. 15(7): 631–8 (1979), FR 2322161, *Izv. Akad. Nauk. SSSR. Ser. Khim*. (12):2808–10 (1973) and *Tetrahedron Lett*. (34): 3707:10 (1968), the teachings of which are incorporated herein by reference.

The invention is illustrated by the following examples which are not intended to be limiting in any way.

EXEMPLIFICATION

Human eosinophils were prepared by isolation from the blood of donor individuals with high levels of circulating blood eosinophils (5–17%) by combining density gradient centifugation and negative selection with anti-CD16 magnetic beads (Hansel, T. T. *J. Immunol. Methods*, 122:97– 103 (1989)). Briefly, the granulocyte fraction from the Percoll centrifugation was incubated with CD16 micro beads (miniMACS, separation unit) for 30 minutes. Cells were then passed through a MACS column (Miltenyi Biotec, Inc., Auburn, Calif.) and eosinophils were collected in the flow through. Eosinophil purity was >996 as determined by analysis of Diff-Quik (Baxter) stained cytocentrifugation preparations by light microscopy.

HL-60 Cells, obtained from the American Type Culture Collection, were resuspended at 0.5 million cells/ml in equal proportions of RPMI-1640 and M199 (Gibco) with 20% fetal calf serum (FCS). After, addition of n-butyric acid (Sigma Chemical Co.) to a final concentration of 0.4 mM, cells were incubated for 4 days at 37° C., 5% $CO_2$ before use in either whole cell chemotaxis assays or preparation for use as membranes for receptor binding assays.

Membrane Preparations for Chemokine Binding and Binding Assays

Membranes were prepared from n-butyric acid-treated HL60 cells. Cells were harvested by centrifugation, washed twice with PBS (phosphate-buffered saline), and the cell pellets were frozen at −70 to −85° C. The frozen pellet was thawed in ice-cold lysis buffer consisting of 5 mM HEPES (N-2-hydroxyethylpiperazine-N'-2-ethane-sulfonic acid) pH 7.5, 2 mM EDTA (ethylenediaminetetraacetic acid), 5 µg/ml each aprotinin, leupeptin, andchymostatin (protease inhibitors), and 100 µg/ml PMSF (phenyl methane sulfonyl fluoride—also a protease inhibitor, at a concentration of 1 to $5×10^7$ cells/ml. This procedure results in cell lysis. The suspension was mixed welL to resuspend all of the frozen cell pellet. Nuclei and cell debris were removed by centrifugation of 400×g for 10 minutes at 4° C. The supernatant was transferred to a fresh tube and the membrane fragments were collected by centrifugation at 25,000×g for 30 minutes at 4° C. The supernatant was aspirated and the pellet was resuspended in freezing buffer consisting of 10 mM HEPES pH 7.5, 300 mM sucrose, 1 µg/ml each aprotinin, leupeptin, and chymostatin, and 10 µg/ml PMSF (approximately 0.1 ml per each $10^8$ cells). All clumps were resolved using a minihomogenizer, and the total protein concentration was determined using a protein assay kit (Bio-Rad, Hercules, Calif., cat #500-0002). The membrane solution was then aliquoted and frozen at −70 to −85° C. until needed.

Binding Assays utilized the membranes described above. Membrane protein (2 to 20 µg total membrane protein) was incubated with 0.1 to 0.2 nM $^{125}$I-labeled RANTES or MIP-1α with or without unlabeled competitor (RANTES or MIP-1α) or various concentrations of compounds. The binding reactions were performed in 60 to 100 µl of a binding buffer consisting of 10 mM HEPES pH 7.2, 1 mM $CaCl_2$, 5 mM $MgCl_2$, and 0.5% BSA (bovine serum albumin), for 60 min at room temperature. The binding reactions were terminated by harvesting the membranes by rapid filtration through glass fiber filters (GF/B or GF/C, Packard) which were presoaked in 0.3% polyethyleneimine. The filters were rinsed with approximately 600 µl of binding buffer containing 0.5 M NaCl, dried, and the amount of bound radioactivity was determined by scintillation counting in a Topcount beta-plate counter.

Chemokines and Chemotaxis.

RANTES and MIP-1α were purchased from Peprotech, Inc. Leukocyte chemotaxis was assessed on eosinophils, peripheral blood mononuclear cells, or HL60 cells differentiated with butyric acid, using a modification of a transendothelial assay (Carr, M. W., et al. T. A., *Proc. Natl Acad Sci, USA*, 91, 3652 (1994)). The endothelial cells used in this assay were the endothelial cell line, ECV 304, obtained from the European collection of Animal Cell Cultures (Porton Downs, Salisbury, U.K.). Endothelial cells were cultured on 6.5 mm diameter Transwell culture inserts (Costar Corp., Cambridge, Mass.) with 3.0 µm pore size. Culture media for the ECV 304 cells consisted of M199+10% FCS, L-glutamine, and antibiotics. The assay media consisted of equal parts RPMI 1640 and M199 with 0.5% BSA. Two hours before the assay, $2×10^5$ ECV 304 cells were plated onto each insert of the 24 well Transwell chemotaxis plate and incubated at 37° C. Chemotactic factors such as RANTES or MIP-1α (Peprotech)(diluted in assay medium) were added to the 24-well tissue culture plates in a final volume of 600 µL. Endothelial-coated Transwells were inserted into each well and $10^6$ cells of the leukocyte type being studied were added to the top chamber in a final volume of 100 µL of assay medium. The plate was then incubated at 37° C. in 5% $CO_2$/95% air for 1–2 h. The cells that had migrated to the bottom chamber were counted using flow cytometry. 500 µL of the cell suspension from the lower chamber was placed in a tube and relative counts were obtained for a set period of time of 30 seconds. This counting method was found to be highly reproducible and enabled gating on the leukocytes and the exclusion of debris or other cells. Counts obtained by this method matched closely those obtained by counting with a microscope. Assays evaluating chemotaxis inhibitors were performed in the same way as control experiments above, except that inhibitor solutions, in assay media containing up to 1% of DMSO cosolvent, were added to both the top and bottom chambers prior to addition of the cells. Inhibitor potency was determined by comparison of cell numbers migrated to the bottom chamber, with or without inhibitor. Control wells contained equivalent amounts of DMSO, but no inhibitor.

Ligand Binding Assay.

$^{125}$I-RANTES and $^{125}$I-MIP-1α were purchased from DuPont-NEN (Boston, Mass.) with a specific activity of 2,200 Ci/mM. Chemokine binding to the target cells, human eosinophils, was carried out using a modification of a method previously reported. (Van Riper, G. S.; *J. Exp. Med.* 177, 851–856 (1993)). Cells were washed once in PEBS and resusupended in binding buffer (50 mM HEPES, 1 mM CaCl$_2$, 5 mM MgCl$_2$, and 0.5% BSA) at a concentration of 1×10$^7$/mL. Aliquots of 50 μL (5×10$^5$ cells) were dispensed into microfuge tubes, followed by the addition of cold and radiolabelled chemokines. The final reaction volume was 200 μL. Nonspecific binding was determined by incubating cells with radiolabeled chemokines in the presence of increasing amounts of (250–500 nM) of cold chemokine. After 60-min incubation, at room temperature, the cells were washed 3× with 1 mL of binding buffer plus 0.5 M NaCl. Cell pellets were then counted. All experiments were carried out using duplicates and repeated at least three times. Curve fit was calculated by Kaleidagraph software (Synergy Software, Reading, Pa.). Inhibition of binding was assessed by the addition of test inhibitor compound at concentrations of 100 μM final concentration, and incubation for 30 min prior to addition of the chemokine as above.

Inhibition of Peripheral Blood Mononuclear Cell (PBMC) Chemotaxis by Compounds L-370 and L-374

Cells were incubated with the concentrations of compound indicated in FIGS. 1A and 1B for 20 minutes at room temperature and were placed in the upper wells of the chemotaxis chambers. Migration in response to MCP-1, RANTES, or MIP-1α was assessed as described above.

FIG. 1A is an illustration of the total number of cells migrating in response to the chemokines with and without preincubation with different concentrations of L-370 or L-374. MCP-1 was used as a negative control to show the specificity of action of the compounds.

FIG. 1B is an illustration of the results of the same experiments as in FIG. 1A, expressed as percentage inhibition, where the inhibition was calculated as cells migrated in the absence of compound/cells migrated in the presence of compound. 100% inhibition of migration occurred with 10.0 μM and 1.0 μM of L-370 and L-374, respectively.

The activities of other test compounds are reported in Tables 1–4 below as RBA, IC$_{50}$ or the inhibitor concentration required for 50% inhibition in receptor binding assays using $^{125}$I-RANTES or $^{125}$MIP-1α as ligand and HL60 cell membranes from cells differentiated by butyric acid (which chemotax in response to RANTES in an almost identical way described for eosinophils).

Leukocyte chemotaxis inhibition is expressed as percent inhibition of RANTES-induced chemotaxis using the same HL60 cells (butyric acid diffentiated) at the indicated concentration (μM) of compound.

TABLE 1

| | | IC50 (μM) | | Chemotaxis Inh |
| --- | --- | --- | --- | --- |
| | L # | Receptor Rantes | Bind. MIP-1α | % Inhib @ μM (HL60) |
| 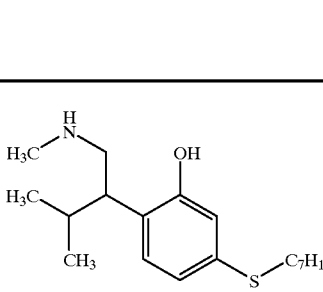 | L-381 | 11 | 12 | 72% @ 2.5 μM<br>100% @ 5 μM |
| 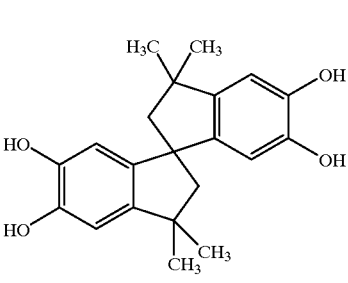 | L-319 | 2.4 | 9 | 31% @ 10 μM |
|  | L-345 | 9 | 12 | 56% @ 8 μM |

TABLE 1-continued
| | L # | IC50 (μM) Receptor Bind. Rantes | IC50 (μM) MIP-1α | Chemotaxis Inh % Inhib @ μM (HL60) |
|---|---|---|---|---|
| 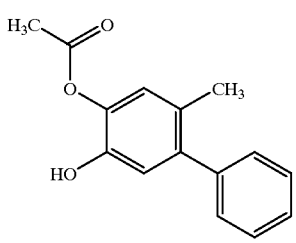 | L-349 | 18 | 10 | not tested |
| 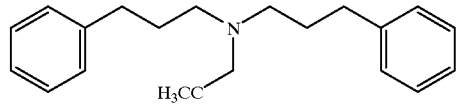 | L-347 | 12 | 7.6 | 21% @ 12 μM<br>90% @ 60 μM |
| 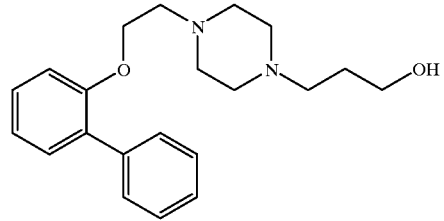 | L-380 | 14 | 8 | not tested |
| 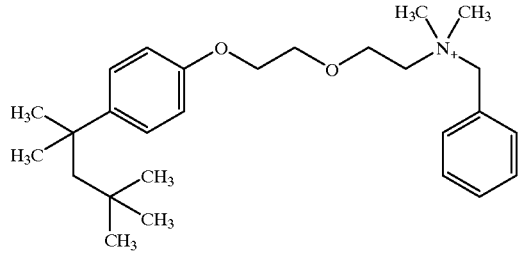 | L-339 | 10 | n.t. | 5% @ 30 μM |
TABLE 2
| | L # | RBA IC50 (μM) Rantes | RBA IC50 (μM) MIP-1α | Inhibition HL60 Chemotaxis % Inhib'n, μM |
|---|---|---|---|---|
| 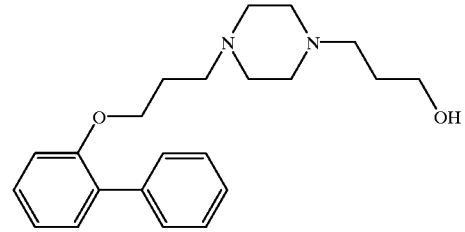 | L-377 | 2 | 0.6 | 66% @ 10 μM |

TABLE 2-continued
| | L # | RBA IC50 (μM) Rantes | MIP-1α | Inhibition HL60 Chemotaxis % Inhib'n, μM |
|---|---|---|---|---|
| 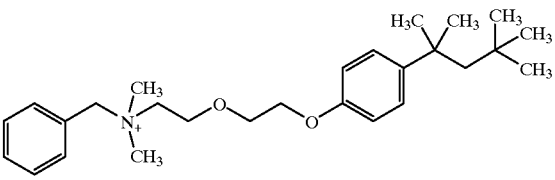 | L-339 | 10 | 23 | not tested |
| 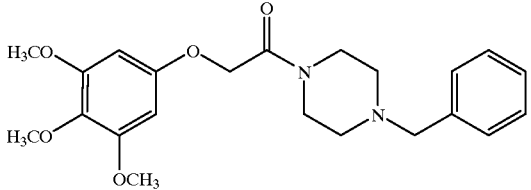 | L-372 | 5.5 | 17 | 89% @ 6 μM |
| 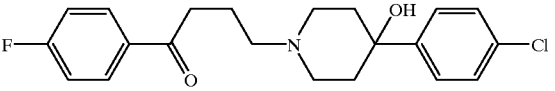 | L-348 | 8 | 10 | 54% @ 4 μM<br>103% @ 20 μM |
| 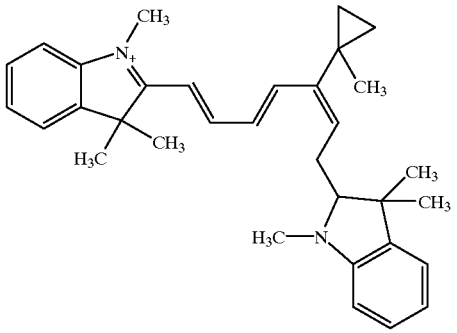 | L-342 | 6 | ≅12 | 74% @ 2 μM |
| 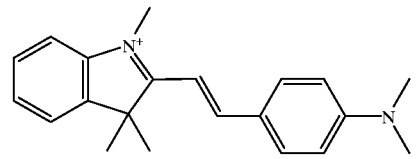 | L-344 | 5 | 15 | 67% @ 2 μM |
| 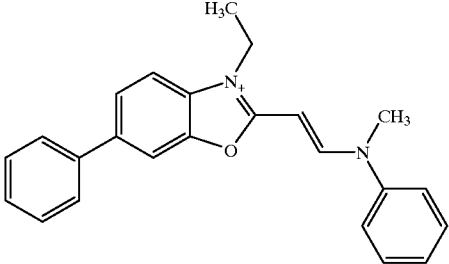 | L-459 | 3 | 13 | 92% @ 15 μM |

TABLE 2-continued
| | L # | RBA IC50 (μM) | | Inhibition HL60 Chemotaxis |
| --- | --- | --- | --- | --- |
| | | Rantes | MIP-1α | % Inhib'n, μM |
| 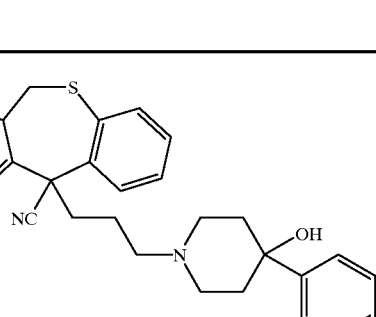 | L-464 | 35 | ≅10 | not tested |
TABLE 3
| | L # | RBA IC50 (μM) | | Leukocyte Chemotaxis (HL60 Cells) |
| --- | --- | --- | --- | --- |
| | | RANTES | MIP-1α | % Inhibition @ μM |
| 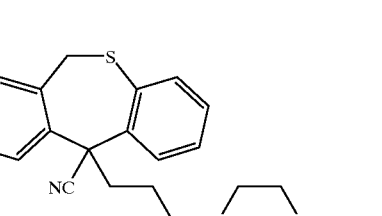 | L-886 | 11.3 | 11.2 | not tested |
| | L-804 | >20 | not tested | not tested |
| 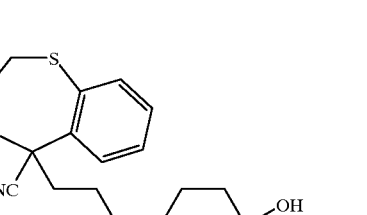 | L-374 | 0.2 | 0.36 | 81% @ 1 μM |

TABLE 3-continued
| | L # | RBA IC50 (μM) | | Leukocyte Chemotaxis (HL60 Cells) |
| | | RANTES | MIP-1α | % Inhibition @ μM |
|---|---|---|---|---|
| 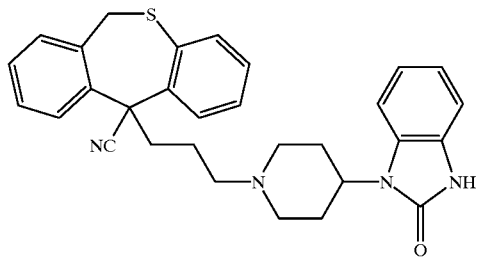 | L-370 | 7.3 | 11.7 | 59% @ 2 μM<br>102% @ 10 μM |
| 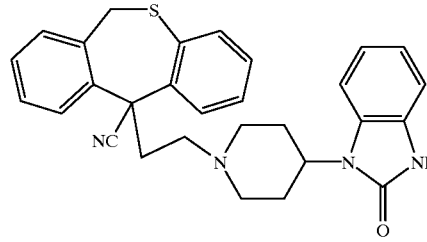 | L-887 | >40 | not tested | not tested |
| 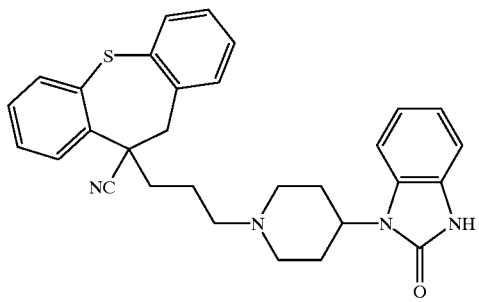 | L-378 | 21 | 33 | not tested |
TABLE 4
INHIBITION OF EOTAXIN-INDUCED EOSINOPHIL CHEMOTAXIS
| | L # | Eosinophil Chemotaxis % inhibition/μM |
|---|---|---|
| 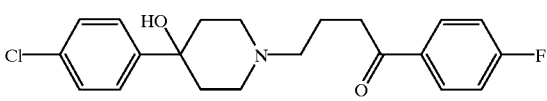 | L-348 | 17%/7 μM<br>86%/35 μM |
| 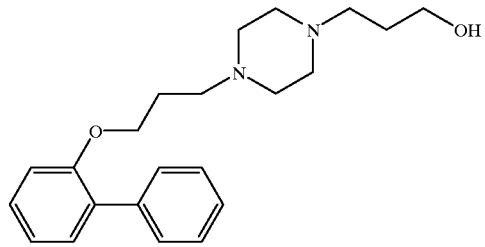 | L-377 | 100%/3 μM<br>100%/6 μM |

TABLE 4-continued

INHIBITION OF EOTAXIN-INDUCED EOSINOPHIL CHEMOTAXIS

| L # | Eosinophil Chemotaxis % inhibition/μM |
|---|---|
| L-370 | 26%/2 μM<br>40%/10 μM |

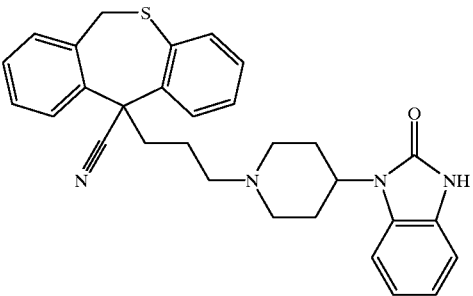

| L-374 | IC50 = 45.5 μM |

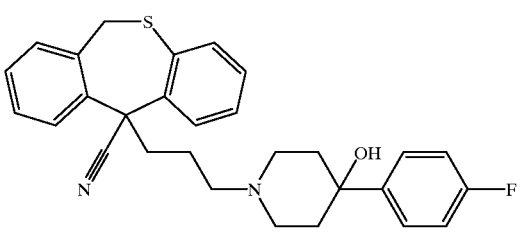

EQUIVALENTS

Those skilled in the art will be able to recognize, or be able to ascertain, using no more than routine experimentation, many equivalents to the specific embodiments of the invention described herein. Such equivalents are intended to be encompassed by the following claims.

What is claimed:

1. A method of treating a subject having a disease associated with aberrant leukocyte recruitment and/or activation, comprising administering to the individual a therapeutically effective amount of a compound represented by the following structural formula:

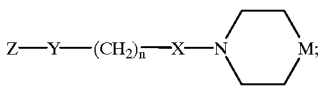

and physiologically acceptable salts thereof, wherein:

M is $>NR_2$, $>CR_1R_2$ or —CO—;

Y is a covalent bond, —O— or —CO—;

n is an integer from one to about five;

X is a covalent bond or —CO—;

$R_1$ is —H, —OH, an aliphatic group, —O-(aliphatic group), —SH or —S-(aliphatic group);

$R_2$ is an aliphatic group, a substituted aliphatic group, an aromatic group, a substituted aromatic group, a benzylic group, a substituted benzylic group, a non-aromatic heterocyclic group or a substituted non-aromatic heterocyclic group; and Z is represented by a structural formula selected from:

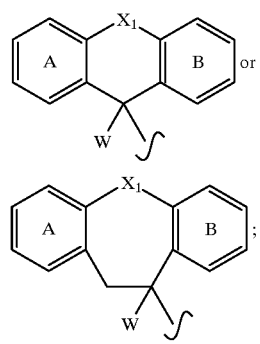

wherein:

$X_1$ is a chemical bond, —S—, —CH$_2$— or —CH$_2$S—;

W is —H or an electron withdrawing group; and wherein Ring A and Ring B are substituted or unsubstituted.

2. The method of claim 1 wherein the compound is represented by the following structural formula:

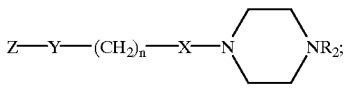

and physiologically acceptable salts thereof.

3. The method of claim 2 wherein —Y— is —O— and —X— is —CO—.

4. The method of claim 3 wherein n is one and $R_2$ is a $C_1$ to about a $C_4$ alkyl group substituted with an aromatic or substituted aromatic group.

5. The method of claim 1 wherein the compound is represented by the following structural formula:

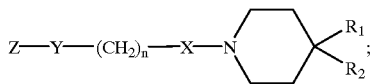

and physiologically acceptable salts thereof, wherein $R_1$ is —H or —OH.

6. The method of claim 5 wherein —Y— is —O— and —X— is —CO—.

7. The method of claim 6 wherein n is one and $R_2$ is $C_1$ to about a $C_4$ alkyl group substituted with an aromatic or substituted aromatic group.

8. The method of claim 2 wherein the compound is represented by the following structural formula:

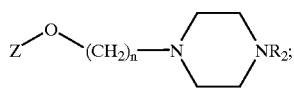

and physiologically acceptable salts thereof.

9. The method of claim 8 wherein n is 2 or 3 and $R_2$ is an aliphatic or substituted aliphatic group.

10. The method of claim 5 wherein the compound is represented by the following structural formula:

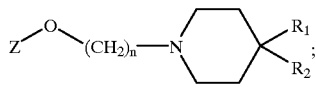

and physiologically acceptable salts thereof, wherein $R_1$ is —H or —OH.

11. The method of claim 10 wherein n is two or three and $R_2$ is an aliphatic or substituted aliphatic group.

12. The method of claim 2 wherein the compound is represented by the following structural formula:

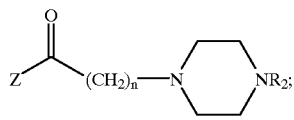

and physiologically acceptable salts thereof.

13. The method of claim 12 wherein n is 3 and $R_2$ is an aromatic group, a substituted aromatic group or an aliphatic group substituted with an aromatic or substituted aromatic group.

14. The method of claim 3 wherein the compound is represented by the following structural formula:

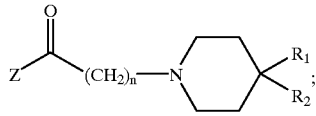

and physiologically acceptable salts thereof.

15. The method of claim 14 wherein n is 3 and $R_2$ is an aromatic group, a substituted aromatic group or an aliphatic group substituted with an aromatic or substituted aromatic group.

16. The method of claim 1 wherein —Y— and —X— are each a covalent bond.

17. The method of claim 1 wherein Z is represented by the following structural formula:

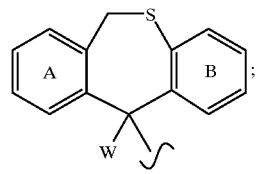

wherein Ring A and/or Ring B are substituted or unsubstituted.

18. The method of claim 17 wherein M is >$NR_2$, >C(OH)$R_2$ or >$CHR_2$.

19. The method of claim 18 wherein n is three and W is —CN.

20. The method of claim 1 wherein Z is represented by the following structural formula:

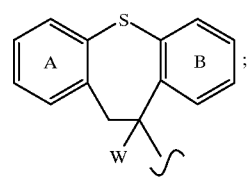

wherein Ring A and/or Ring B are substituted or unsubstituted.

21. The method of claim 20 wherein M is >C(OH)$R_2$ or >$CHR_2$.

22. The method of claim 21 wherein W is —CN and n is three.

23. The method of claim 1 wherein:

—X— and —Y— are each a covalent bond;

W is —H, —CN, alkylsulfonyl, carboxamido or carboxyalkyl;

n is an integer from 2–5;

Ring A is substituted with $R_8$ and $R_9$, wherein $R_8$ and $R_9$ are independently —H, a halogen, alkoxy or alkyl, or, taken together with ring A, form a naphthyl group;

M is >CH—OH, >C(OH)$R_6$, >CH—$R_7$, >C=O or >$NR_5$;

$R_5$ is alkanoyl, aroyl, aralkoyl, alkyl, aralkyl or cycloalkyl;

$R_6$ is an aryl group; and $R_7$ is a heterocylic ring.

24. The method of claim 1 wherein the compound is represented by the structural formula:

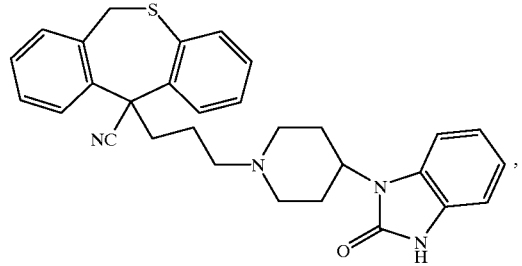

or a physiologically acceptable salt thereof.

25. The method of claim 1 wherein the compound is represented by the structural formula:

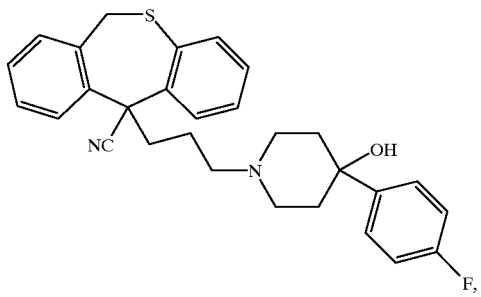

or a physiologically acceptable salt thereof.

26. A method of treating a subject having a disease associated with aberrant leukocyte recruitment and/or activation, said disease being selected from the group consisting of arthritis, psoriasis, multiple sclerosis, ulcerative colitis, Crolin's disease, allergy, asthma, AIDS associated encephalitis, AIDS related maculopapular skin eruption, AIDS related interstitial pneumonia, AIDS related enteropathy, AIDS related periportal hepatic inflammation and AIDS related glomerulo nepliritis, comprising administering to the individual a therapeutically effective amount of a compound represented by the following structural formula:

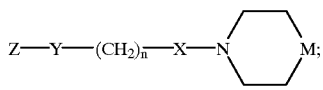

and physiologically acceptable salts thereof, wherein:

M is >NR$_2$, >CR$_1$R$_2$ or —CO—;

R$_1$ is —H, —OH, an aliphatic group, —O-(aliphatic group), —SH or —S-(aliphatic group); and R$_2$ is an aliphatic group, a substituted aliphatic group, an aromatic group, a substituted aromatic group, a benzylic group, a substituted benzylic group, a non-aromatic heterocyclic group or a substituted non-aromatic heterocyclic group; and Z is represented by a structural formula selected from:

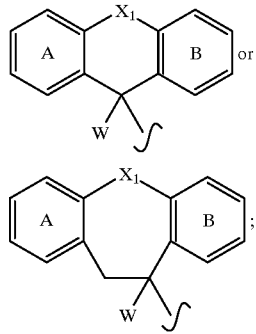

wherein:

X$_1$ is a chemical bond, —S—, —CH$_2$— or —CH$_2$S—;

W is —H or an electron withdrawing group; and wherein Ring A and Ring B are substituted or un substituted.

27. The method of claim 26 wherein said disease is ulcerative colitis or Crohn's disease.

28. A method of treating a subject having a disease associated with aberrant leukocyte recruitment and/or activation, comprising administering to the individual a therapeutically effective amount of a compound represented by the following structural formula:

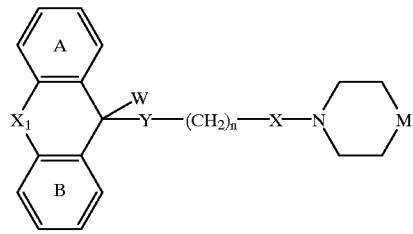

and physiologically acceptable salts thereof, wherein:

Ring A and Ring B are each, independently, substituted or unsubstituted;

X$_1$ is —CH$_2$CH$_2$—, —CH$_2$S— or —S—;

W is —H or an electron withdrawing group;

Y is a covalent bond, —O— or —CO—;

n is an integer from one to about five;

X is a covalent bond or —CO—,

M is >NR$_2$, >CR$_1$R$_2$ or >C=O;

R$_1$ is —H, —OH, an aliphatic group, —O-(aliphatic group), —SH or —S-(aliphatic group); and R$_2$ is an aliphatic group, a substituted aliphatic group, an aromatic group, a substituted aromatic group, a benzylic group, a substituted benzylic group, a non-aromatic heterocyclic group or a substituted non-aromatic heterocyclic group.

29. The method of claim 28 wherein X and Y are each a covalent bond.

30. The method of claim 28 wherein said disease is selected from the group consisting of arthritis, psoriasis, multiple sclerosis, ulcerative colitis, Crohn's disease, allergy, asthma, AIDS associated encephalitis, AIDS related maculopapilar skin eruption, AIDS related interstitial pneumonia, AIDS related enteropathy, AIDS related periportal hepatic inflammation and AIDS related glomerulo nephritis.

31. A method of treating a subject having a disease associated with aberrant leukocyte recruitment and/or activation, comprising administering to the individual a therapeutically effective amount of a compound that can inhibit the binding of a chemokine to a chemokine receptor, wherein the compound is represented by the following structural formula:

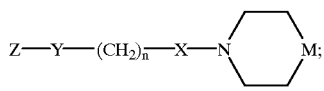

and physiologically acceptable salts thereof, wherein:

M is >NR$_2$, >CR$_1$R$_2$ or >C=O;

Y is a covalent bond, —O— or —CO—;

n is an integer from one to about five;

X is a covalent bond or —CO—;

R₁ is —H, —OH, an aliphatic group, —O-(aliphatic group), —SH or —S-(aliphatic group);

R₂ is an aliphatic group, a substituted aliphatic group, an aromatic group, a substituted aromatic group, a benzylic group, a substituted benzylic group, a non-aromatic heterocyclic group or a substituted non-aromatic heterocyclic group; and Z is represented by a structural formula selected from:

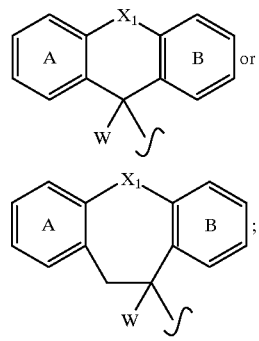

wherein:

X₁ is a chemical bond, —S—, —CH₂— or —CH₂S—;

W is —H or an electron withdrawing group; and wherein ring A and ring B are substituted or unsubstituted.

32. The method of claim 31 wherein said chemokine is MIP-1α or RANTES.

33. A method of treating a subject having a disease associated with aberrant leukocyte recruitment and/or activation, comprising administering to the individual a therapeutically effective amount of a compound that can inhibit the binding of a chemokine to a chemokine receptor, wherein the compound is represented by the following structural formula:

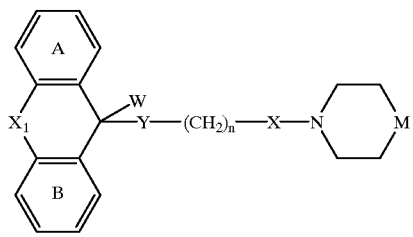

and physiologically acceptable salts thereof, wherein:

Ring A and Ring B are each, independently, substituted or unsubstituted,

X₁ is —CH₂CH₂—, —CH₂S— or —S—;

W is —H or an electron withdrawing group;

Y is a covalent bond, —O— or —CO—;

n is an integer from one to about five;

X is a covalent bond or —CO—;

M is >NR₂, >CR₁R₂ or >C=O;

R₁ is —H, —OH, an aliphatic group, —O-(aliphatic group), —SH or —S-(aliphatic group); and R₂ is an aliphatic group, a substituted aliphatic group, an aromatic group, a substituted aromatic group, a benzylic group, a substituted benzylic group, a non-aromatic heterocyclic group or a substituted non-aromatic heterocyclic group.

34. The method of claim 33 wherein said chemokine is MIP-1α or RANTES.

35. The method of claim 33 wherein said disease is selected from the group consisting of arthritis, psoriasis, multiple sclerosis, Crohn's disease, AIDS associated encephalitis, AIDS related maculopapular skin eruption, AIDS related interstitial pneumonia, AIDS related enteropathy, AIDS related periportal hepatic inflammation and AIDS related glomerulo nephritis.

36. The method of claim 33 wherein said disease is selected from the group consisting of ulcerative colitis, allergy and asthma.

* * * * *